(12) United States Patent
Lee et al.

(10) Patent No.: US 7,138,091 B2
(45) Date of Patent: Nov. 21, 2006

(54) REACTION CUVETTE HAVING ANTI-WICKING FEATURES FOR USE IN AN AUTOMATIC CLINICAL ANALYZER

(75) Inventors: Ching-Cherng Lee, Newark, DE (US); Thai Huynh-Ba, Newark, DE (US); Donald Richard Phillips, Sr., Newark, DE (US); Timothy Patrick Evers, Wilmington, DE (US)

(73) Assignee: Dade Behring Inc., Deerfield, IL (US)

( * ) Notice: Subject to any disclaimer, the term of this patent is extended or adjusted under 35 U.S.C. 154(b) by 387 days.

(21) Appl. No.: 10/623,436

(22) Filed: Jul. 18, 2003

(65) Prior Publication Data

US 2005/0013746 A1    Jan. 20, 2005

(51) Int. Cl.
*B01L 3/02* (2006.01)

(52) U.S. Cl. .................. 422/102; 422/55; 422/73; 422/99; 436/165; 436/172; 356/244; 356/246

(58) Field of Classification Search .............. 422/73, 422/82.05, 82.08, 82.09, 99, 102, 55; 436/165, 436/172; 356/244, 246, 335–338
See application file for complete search history.

(56) References Cited

U.S. PATENT DOCUMENTS

| | | | | |
|---|---|---|---|---|
| 3,554,705 A | * | 1/1971 | Johnston | 422/61 |
| 3,627,432 A | * | 12/1971 | Bergmann | 356/246 |
| 3,998,594 A | * | 12/1976 | Horne | 422/82.09 |
| 4,229,104 A | * | 10/1980 | Lahme et al. | 356/246 |
| 4,373,812 A | | 2/1983 | Stein et al. | |
| 4,560,269 A | * | 12/1985 | Baldszun et al. | 356/246 |
| 4,762,798 A | * | 8/1988 | Deutsch | 436/67 |
| 4,847,050 A | * | 7/1989 | Jenkins et al. | 422/102 |
| 4,902,479 A | | 2/1990 | Bri kus | |
| 5,098,661 A | * | 3/1992 | Froehlich et al. | 422/102 |
| 5,437,841 A | | 8/1995 | Balmer | |
| 5,571,479 A | | 11/1996 | Koch | |
| 5,658,532 A | | 8/1997 | Kurosaki et al. | |
| 5,840,256 A | * | 11/1998 | Demers et al. | 422/102 |
| 6,027,695 A | * | 2/2000 | Oldenburg et al. | 422/102 |
| 6,108,080 A | * | 8/2000 | Kloth | 356/244 |
| 6,157,456 A | | 12/2000 | Hvass et al. | |
| 6,214,626 B1 | | 4/2001 | Meller et al. | |
| 6,249,345 B1 | | 6/2001 | Kraack et al. | |
| 6,333,007 B1 | | 12/2001 | Svensson et al. | |
| 6,752,967 B1 | * | 6/2004 | Farina et al. | 422/102 |
| 6,767,607 B1 | * | 7/2004 | Tanner et al. | 428/131 |

* cited by examiner

*Primary Examiner*—Jill Warden
*Assistant Examiner*—Dwayne K. Handy
(74) *Attorney, Agent, or Firm*—Leland K. Jordan

(57) ABSTRACT

A reaction cuvette having anti-wicking wall fillets that inhibit liquid wicking along an interior wall surface so that the reaction cuvette may be used in a cuvette-rewashing system in an automated analyzer and not be adversely affected by any reagent contaminants remaining from assays previously performed in said reaction cuvette. The anti-wicking wall fillets comprise a curvilinear taper extending from an open top downwards into the cuvette to form a rounded concave blend between the cuvette's front and back walls and side walls.

2 Claims, 16 Drawing Sheets

REACTION CUVETTE HAVING ANTI-WICKING FEATURES FOR USE IN AN AUTOMATIC CLINICAL ANALYZER

FIELD OF THE INVENTION

The present invention relates to an apparatus for automatically processing a patient's biological fluids such as urine, blood serum, plasma, cerebrospinal fluid and the like. In particular, the present invention provides a reaction cuvette in which liquid wicking upwards along interior walls is minimized.

BACKGROUND OF THE INVENTION

Various types of tests related to patient diagnosis and therapy can be performed by analysis assays of a sample of a patient's infections, bodily fluids or abscesses. Such patient samples are typically placed in sample vials, extracted from the vials, combined with various reagents in special reaction cuvettes or tubes, incubated, and analyzed to aid in treatment of the patient. In typical clinical chemical analyses, one or two assay reagents are added at separate times to a liquid sample, the sample-reagent combination is mixed and incubated within a reaction cuvettes. Analytical measurements using a beam of interrogating radiation interacting with the sample-reagent combination, for example turbidimetric or fluorometric or absorption readings or the like, are made to ascertain end-point or rate values from which an amount of analyte may be determined using well-known calibration techniques.

Although various known clinical analyzers for chemical, immunochemical and biological testing of samples are available, analytical clinical technology is challenged by increasing needs for improved levels of analysis. Due to increasing pressures on clinical laboratories to reduce cost-per-reportable result, there continues to be a need for improvements in the overall cost performance of automated clinical analyzers. In particular, sample analysis continuously needs to be more cost effective in terms of reducing consumables or the cost thereof required for each and every reaction assay.

A positive contributor to reducing cost-per-reportable result is the ability to repeatedly perform reaction assays in reaction cuvettes that are washed or otherwise cleaned after a first reaction is completed and between subsequent reaction assays. What has been overlooked, however, in many such cleaning systems, is that washing techniques are not fully capable of restoring a cleaned used cuvette to the degree of cleanliness of an unused cuvette, most especially if reagent residues from a preceding assay have wicked upwards along an inside wall of the reaction cuvette onto its top surface or even onto an outside surface. Thus, for reaction cuvettes to be useful in a cuvette-rewashing system, it is advantageous that capillary wicking, a process in which fluids inside a cuvette flow upwards along interior walls, be totally eliminated or significantly minimized. In addition, elimination of wicking positively contributes to the accuracy of reaction assay measurements because the integrity of the reagents and sample originally dispersed into the cuvette is maintained; i.e., no liquids have capillary wicked out of the original mixture so that integrity of the reaction constituents is maintained.

U.S. Pat. No. 4,902,479 discloses use of a barrier structure extending along the surface of a cover member to inhibit premature mixing of constituents inside proximate chambers due to wicking movement of constituents stored in one chamber.

U.S. Pat. No. 5,571,479 discloses an analysis cuvette in which plane-parallel side-walls and the bottom of the cuvette which are used as measuring windows for spectrophotometrical absorbance and fluorescence polarization measurements of the cuvette's contents.

U.S. Pat. No. 5,658,532 discloses an analysis cuvette having a rectangular top portion on the top, a cylindrical portion below the top portion, and a lower rectangular portion so as to not unfavorably rotate when measuring the absorption of light transmitted through the cuvette's contents.

U.S. Pat. No. 6,214,626 discloses an analysis cuvette which permits simultaneous use as reaction vessel for taking up one or more reaction liquids, for incubating and storing these liquids and for carrying out optical measurements so that analysis may be free of carryover.

U.S. Pat. No. 6,249,345 discloses an analysis cuvette having pairs of planar-parallel optical windows opposite one another, wherein the distance between one pair is different from the distance of another pair in order to make available differing layer thickness of the sample fluid for measurements of the cuvette's contents.

SUMMARY OF THE INVENTION

The principal object of the invention is to provide an improved reaction cuvette having features to inhibit liquid wicking along an interior wall surface so that the reaction cuvette may be used in a cuvette-rewashing system in an automated analyzer and not be adversely affected by any reagent contaminants remaining from assays previously performed in said reaction cuvette. This is achieved in the present invention by the addition of anti-wicking wall fillets comprising a curvilinear taper extending from an open top downwards into the cuvette having the shape of a variable blend radius between the front and back walls and side walls of the cuvette. The variable blend radius of each anti-wicking wall fillet gradually increases from a lower region to the top inner section of the cuvette. In addition, the reaction cuvette has surface features that do not interfere with the integrity of a beam of interrogating radiation interacting with the sample-reagent combination contained therein. Other features may optionally be included to facilitate automated handling of a such a reaction cuvette.

BRIEF DESCRIPTION OF THE DRAWINGS

The invention will be more fully understood from the following detailed description thereof taken in connection with the accompanying drawings which form a part of this application and in which.

DETAILED DESCRIPTION OF THE INVENTION

Figure 1:
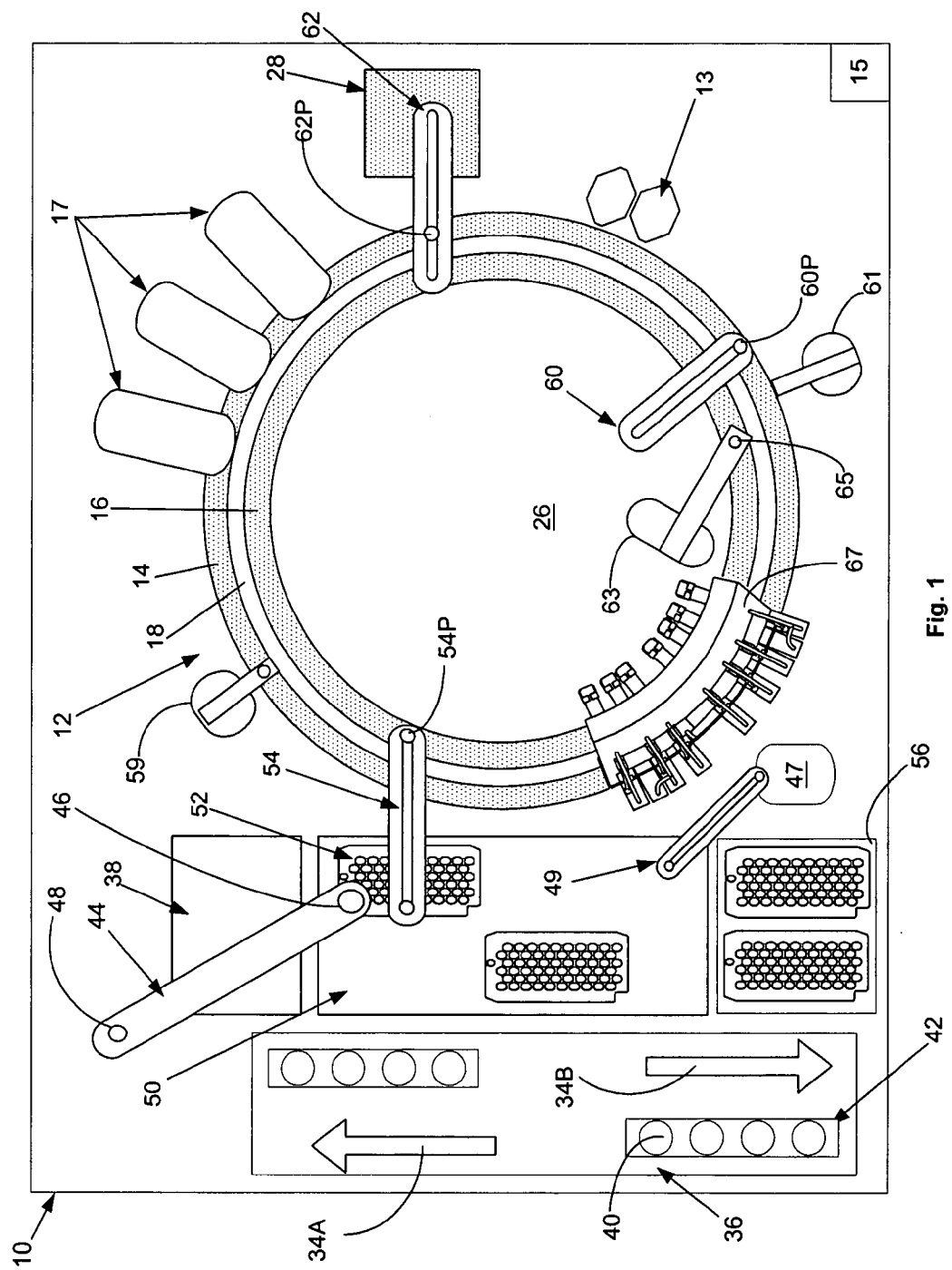
FIG. 1 is a schematic plan view of an automated analyzer in which the present invention may be employed to advantage.
Figure 2:
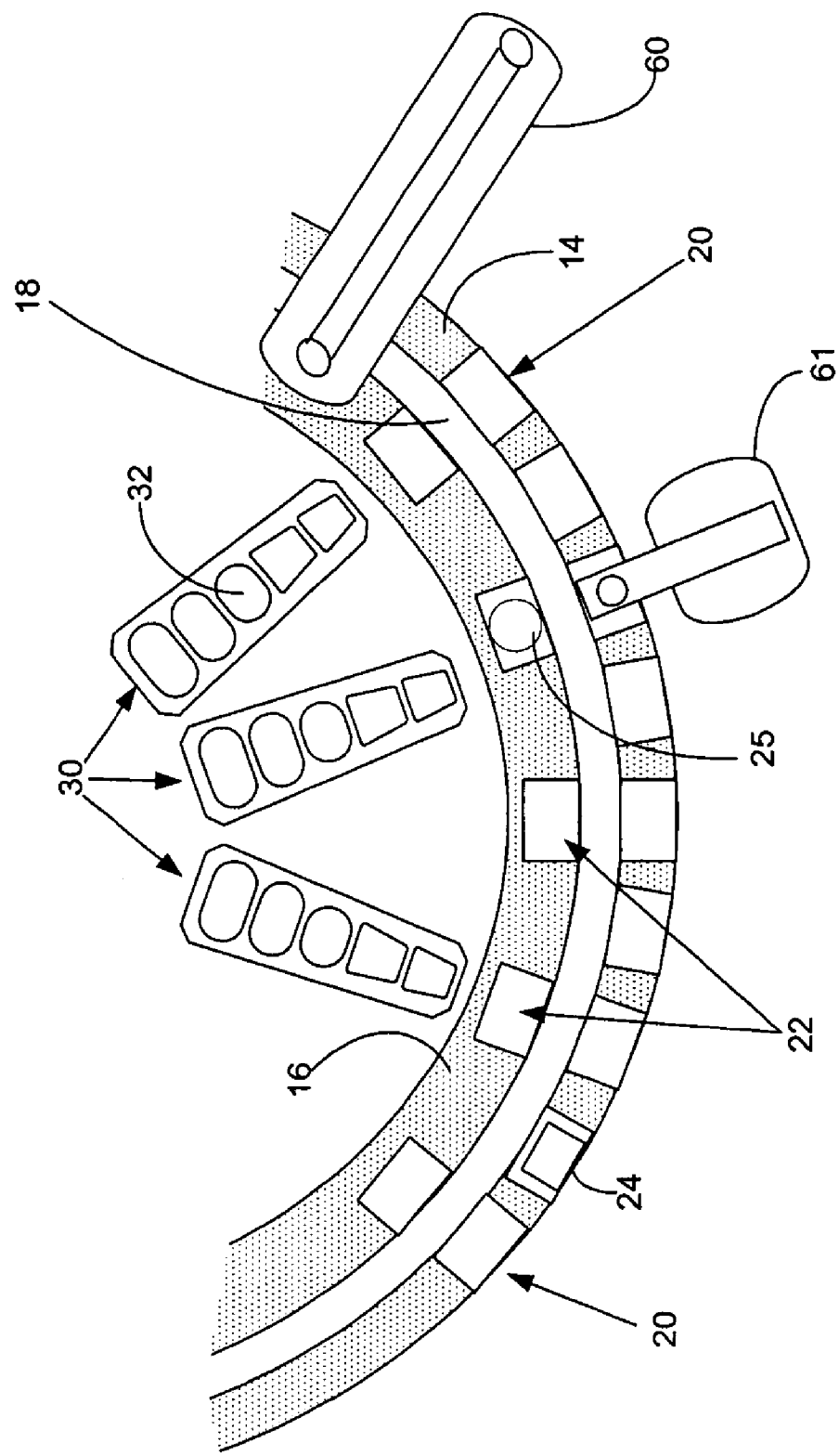
FIG. 2 is an enlarged schematic plan view of a portion of the analyzer of FIG. 1.

FIG. 1, taken with FIG. 2, shows schematically the elements of an automatic chemical analyzer 10 in which the present invention may be advantageously practiced, analyzer 10 comprising a reaction carousel 12 supporting an outer cuvette carousel 14 having cuvette ports 20 formed therein and an inner cuvette carousel 16 having vessel ports 22 formed therein, the outer cuvette carousel 14 and inner cuvette carousel 16 being separated by a open groove 18. Cuvette ports 20 are adapted to receive a plurality of reaction cuvettes 24 that contain various reagents and sample liquids for conventional clinical and immunoassay assays while vessel ports 22 are adapted to receive a plurality of reaction vessels 25 that contain specialized reagents for ultra-high sensitivity luminescent immunoassays. Reaction carousel 12 is rotatable using stepwise movements in a constant direction, the stepwise movements being separated by a constant dwell time during which carousel 12 is maintained stationary and computer controlled assay operational devices 13, such as sensors, reagent add stations, mixing stations and the like, operate as needed on an assay mixture contained within a cuvette 24.

Analyzer 10 is controlled by software executed by the computer 15 based on computer programs written in a machine language like that used on the Dimension® clinical chemistry analyzer sold by Dade Behring Inc, of Deerfield, Ill., and widely used by those skilled in the art of computer-based electromechanical control programming. Computer 15 also executes application software programs for performing assays conducted by various analyzing means 17 within analyzer 10.

Temperature-controlled reagent storage areas 26 and 28 store a plurality of multi-compartment elongate reagent cartridges 30 like that described in co-pending application Ser. No. 09/949,132 assigned to the assignee of the present invention, and containing reagents in wells 32 as necessary to perform a given assay.

A bidirectional incoming and outgoing sample tube transport system 36 having input lane 34A and output lane 34B transports incoming individual sample tubes 40 containing liquid specimens to be tested and mounted in sample tube racks 42 into the sampling arc of a liquid sampling arm 44. Liquid specimens contained in sample tubes 40 are identified by reading bar coded indicia placed thereon using a conventional bar code reader to determine, among other items, a patient's identity, the tests to be performed, if a sample aliquot is to be retained within analyzer 10 and if so, for what period of time. It is also common practice to place bar coded indicia on sample tube racks 42 and employ a large number of bar code readers installed throughout analyzer 10 to ascertain, control and track the location of sample tubes 40 and sample tube racks 42.

Figure 3:
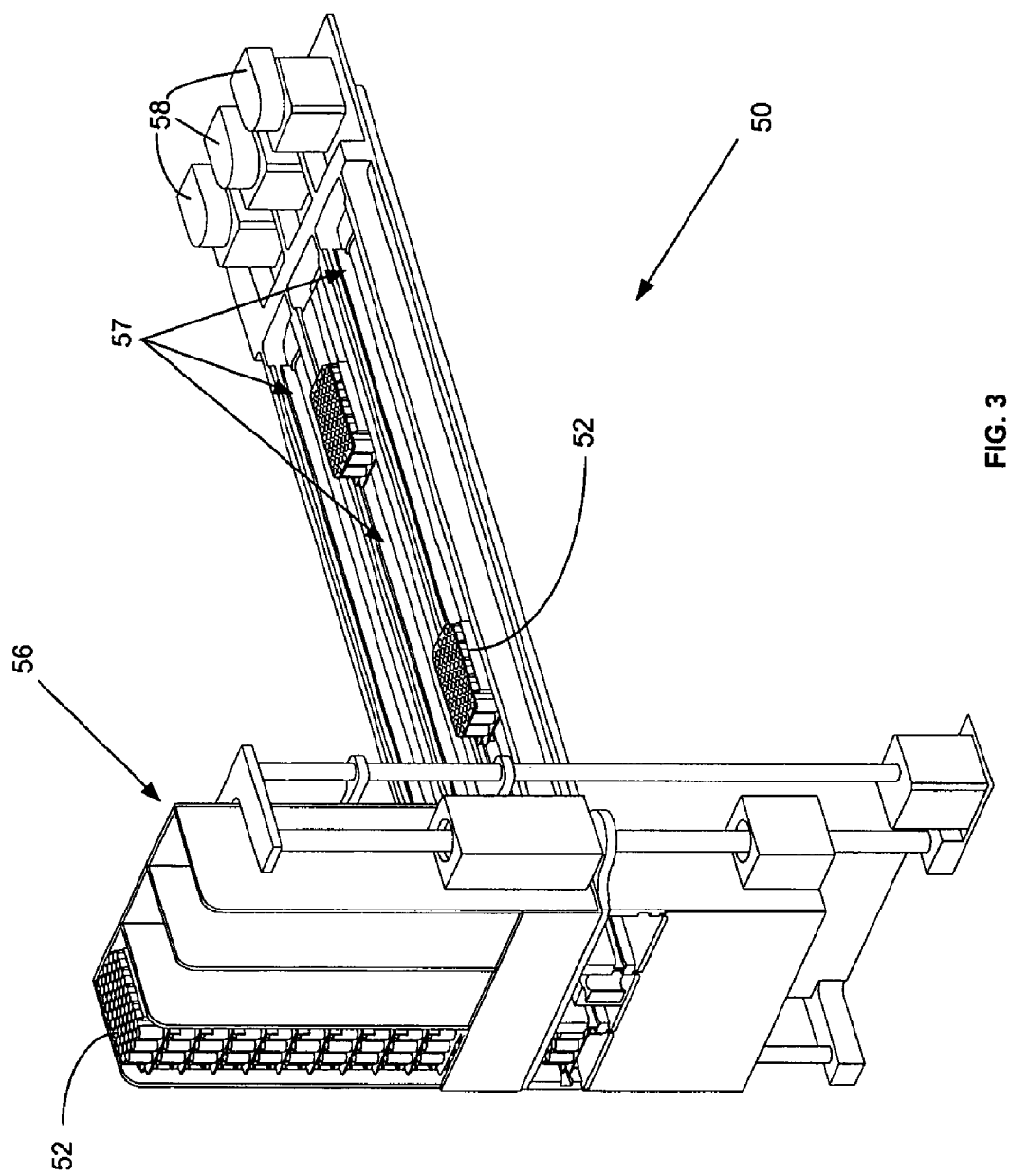
FIG. 3 is a perspective elevation view of an automated aliquot vessel array storage and handling unit.
Figure 4:
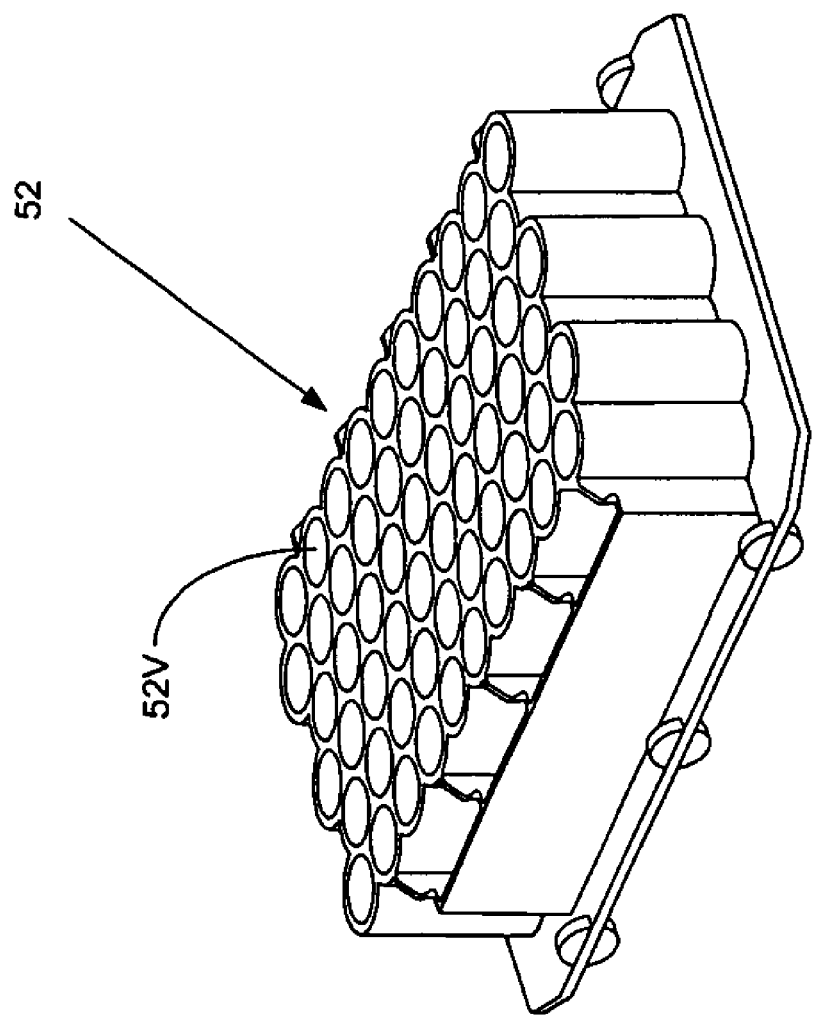
FIG. 4 is perspective elevation view of an aliquot vessel array.

Sampling arm 44 supports a liquid sampling probe 46 mounted to a rotatable shaft 48 so that movement of sampling arm 44 describes an arc intersecting the sample tube transport system 36 and an aliquot vessel array transport system 50, as seen in FIG. 3. Sampling arm 44 is operable to aspirate liquid sample from sample tubes 40 and to dispense an aliquot sample into one or more of a plurality of vessels 52V in aliquot vessel array 52, as seen in FIG. 4, depending on the quantity of sample required to perform the requisite assays and to provide for a sample aliquot to be retained by analyzer 10 within environmental chamber 38. A conventional ion selective electron measuring station 47 equipped with a conventional ion selective electron probe 49 may be conveniently located proximate aliquot vessel array transport system 50 in order to conduct ionic analyte measurements on sample aliquots aspirated from vessels 52V by probe 49 and dispensed into the ion selective electron measuring station 47.

Aliquot vessel array transport system 50 comprises an aliquot vessel array storage and dispense module 56 and a number of linear drive motors 58 adapted to bi-directionally translate aliquot vessel arrays 52 within a number of aliquot vessel array tracks 57 below a sample aspiration and dispense arm 54 located proximate reaction carousel 12. Sample aspiration and dispense arm 54 is controlled by computer 15 and is adapted to aspirate a controlled amount of sample from individual vessels 52V positioned at a sampling location within a track 57 using a conventional liquid probe 54P and then shuttle liquid probe 54P to a dispensing location where an appropriate amount of aspirated sample is dispensed into one or more cuvettes 24 in cuvette ports 20 for testing by analyzer 10 for one or more analytes. Prior to testing by analyzer 10, a portion of sample may be aspirated by ion probe 49 and deposited within an empty cuvette 24 in order to determine if the sample might produce an erroneous assay due to inherent sample absorbance (e.g., interfering icterus, lipemia or hemolysis) and the test result so denoted the presence of interfering icterus, lipemia or hemolysis may be determined by diluting the sample using ion probe 49 and then exposing a diluted sample to interrogating radiation equipped with appropriate chromatic filters and measured using a photosensor to conduct a colormetric analysis known in the art. Ion probe 49 may also be used for a similar dilution of plasma protein samples. After sample has been dispensed into reaction cuvettes 24, conventional transfer means move aliquot vessel arrays 52 as required between aliquot vessel array transport system 50, environmental chamber 38 and a disposal area, not shown.

A number of reagent aspiration and dispense arms 60 and 62 comprising a pair of conventional liquid reagent probes, 60P and 62P, respectively, are independently mounted and translatable between reagent storage areas 26 and 28, respectively. Probes 60P and 62P comprise conventional mechanisms for aspirating reagents required to conduct specified assays at a reagenting location from wells 32 in an appropriate reagent cartridge 30, the probes 60P and 62P subsequently being shuttled to a reagent dispensing location where reagent(s) are dispensed into reaction cuvettes 24. A number of reagent cartridges 30 are inventoried in controlled environmental conditions inside reagent storage areas 26 and 28; a key factor in maintaining high assay throughput is the ability to quickly and accurately shuttle reagent cartridges 30 inside reagent storage areas 26 and 28 to reagenting locations for access by probes 60P and 62P.

Reaction cuvette load station 61 and reaction vessel load station 63 are respectively positioned proximate outer cuvette carousel 14 and inner vessel carousel 16 and are adapted to load reaction cuvettes 24 into cuvette ports 20 sideways as described later and reaction vessels 25 into vessel ports 22 using for example a sliding chute 65. In operation, used cuvettes 24 in which an assay has been finally conducted, are washed and dried in a wash station 67 like disclosed in co-pending application Ser. No. 10/623,360 assigned to the assignee of the present invention. Subsequent assays are conducted in cleaned used cuvettes 24 unless dictated otherwise for reasons like disclosed in co-pending application Ser. No. 10/318,804 assigned to the assignee of the present invention. Cuvette unload station 59 is adapted to remove unusable reaction cuvettes 24 from cuvette ports 20 again using a translatable robotic arm 65 like seen on load stations 61 and 63.

Figure 5:
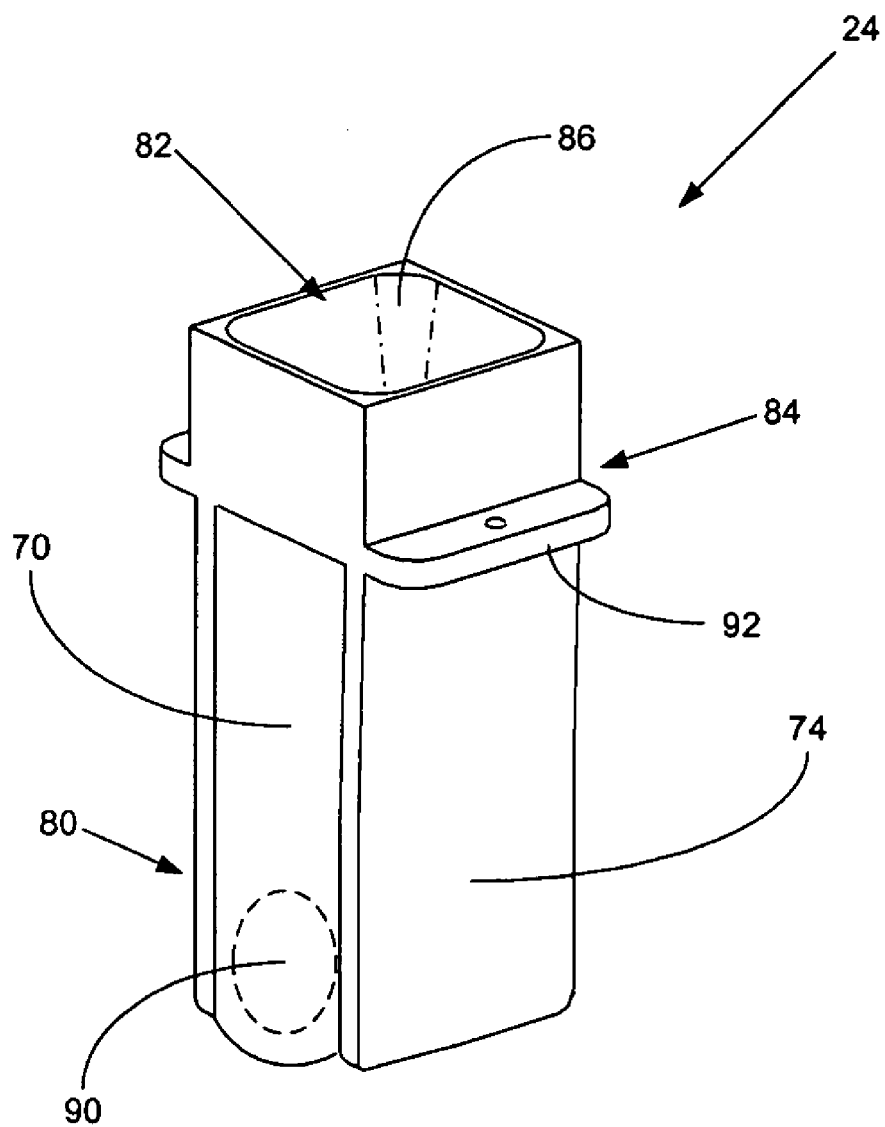
FIG. 5 is perspective view of a reaction cuvette illustrative of the present invention and useful in the analyzer of FIG. 1.
Figure 6:
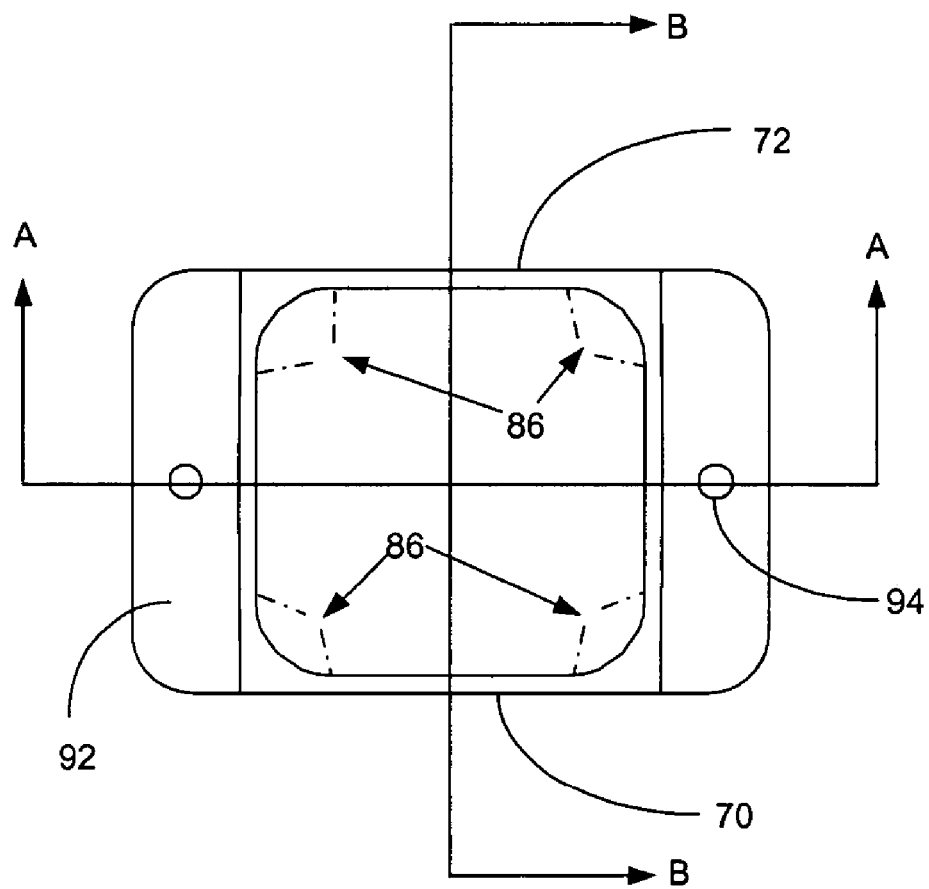
FIG. 6 is a top plan view of the reaction cuvette of FIG. 5.
Figure 6A:
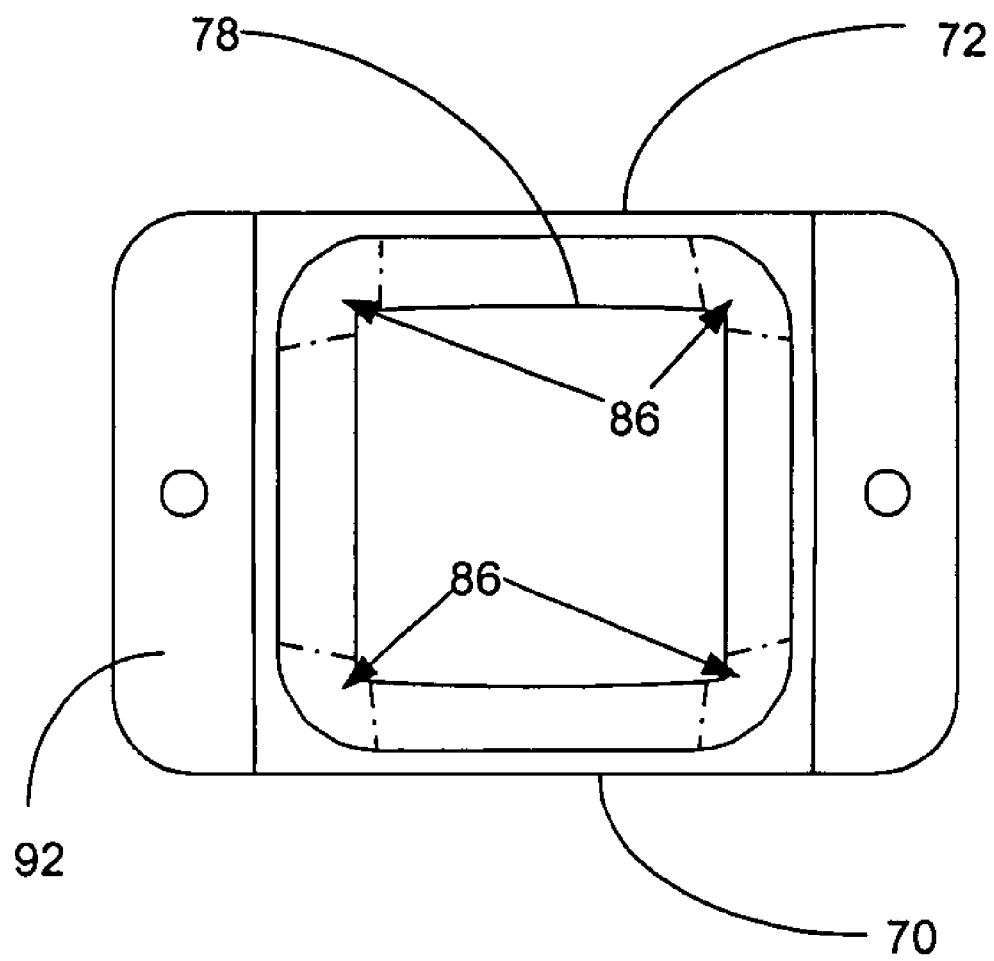
FIG. 6A is a simplified top plan view of the reaction cuvette of FIG. 5.
Figure 7:
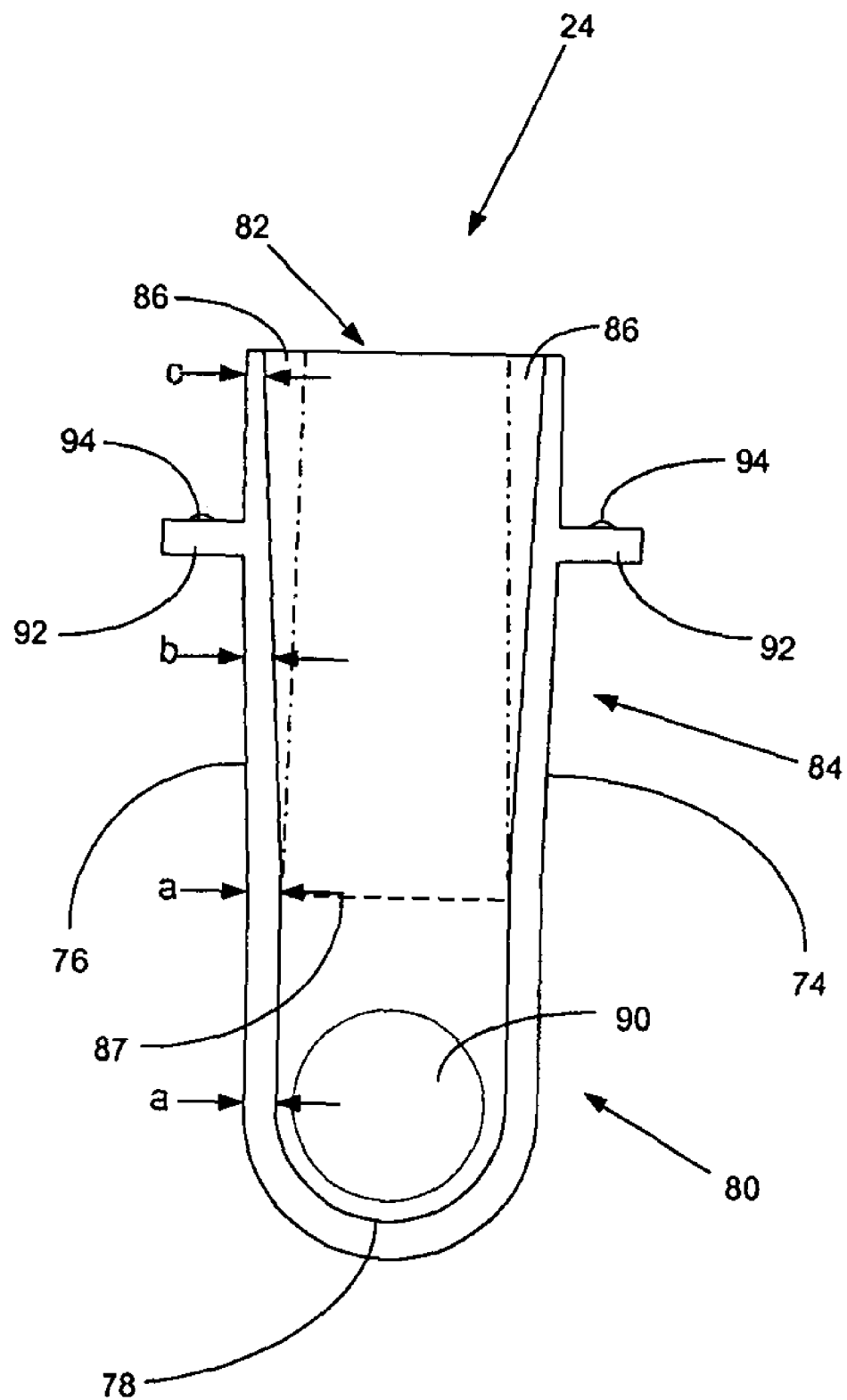
FIG. 7 is a section view of the reaction cuvette of FIG. 6 along the lines A—A.
Figure 7A:
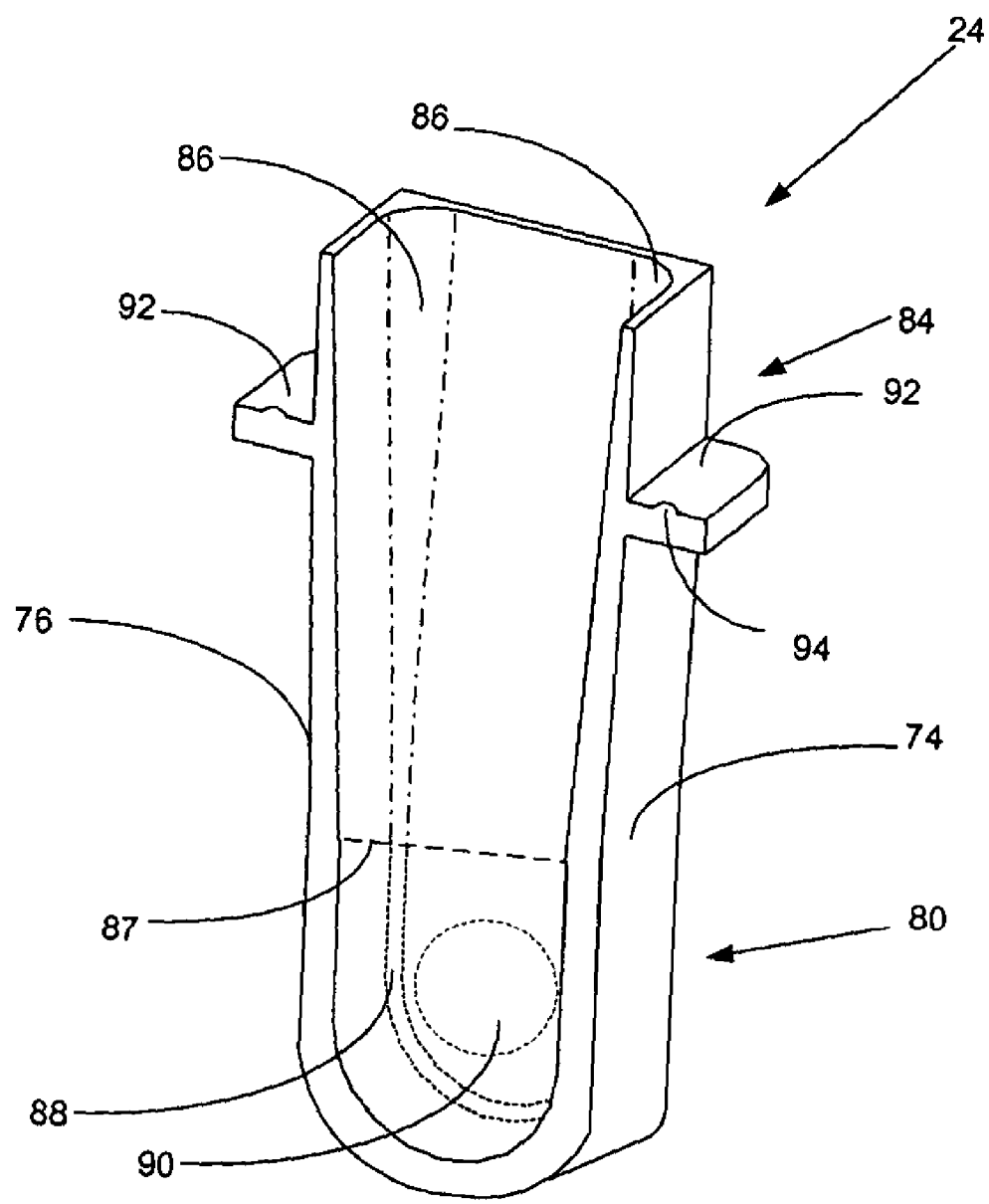
FIG. 7A is a perspective view of the section view of FIG. 7.
Figure 8:
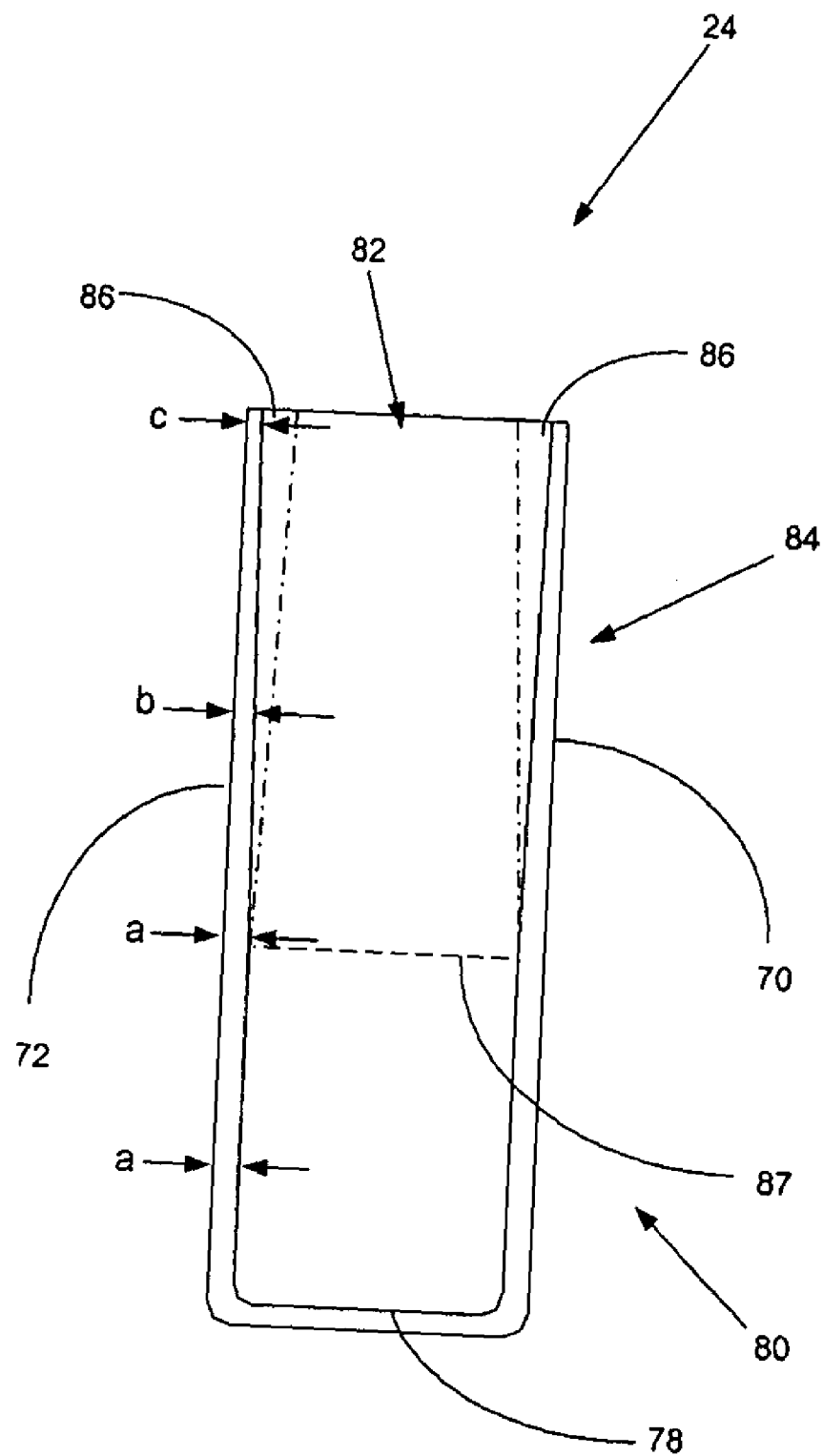
FIG. 8 is a section view of the reaction cuvette of FIG. 6 along the lines B—B.

The reaction cuvette 24 shown in FIGS. 5 to 8 exemplifies a first embodiment of the present invention as comprising an essentially rectangular box-shaped part 24 with a mutually opposed front wall 70 and back wall 72 (FIGS. 5 and 8) perpendicular to and separating two mutually opposed side walls 74 and 76 (FIGS. 5 and 7). FIG. 5 is a external isometric view of reaction cuvette 24 illustrating a generally rectangular lower section 80 supporting an open top section 84 of cuvette 24. FIG. 6 is a top plan view showing a pair of projecting ledges 92 on opposing sides of cuvette 24, each ledge 92 having a latching bulge 94 formed therein. FIG. 6A is a simplified top plan view showing the bottom surface 78 of lower section 80. FIG. 7 is a cross-section view taken along lines A—A of FIG. 6 and FIG. 8 is a cross-section view along lines B—B of FIG. 6. FIG. 7A is a perspective view of the cross-section view of FIG. 7. A curved bottom surface 78 disposed between front wall 70 and back wall 72 integrates side walls 74 and 76 together as best seen in FIG. 7A and closes the lower inner section 80 of reaction cuvette 24. A top opening 82 is defined in the top inner section 84 of cuvette 24 by the uppermost portions of front wall 70, back wall 72 and side walls 74 and 76 thereby allowing liquids to be freely dispensed into cuvette 24. The thickness of front wall 70, back wall 72, and side walls 74 and 76 is generally uniform within the lower inner section 80 but gradually decreases as described hereinafter between the junction between lower inner section 80 and the top inner section 84 of cuvette 24, indicated by dashed line 87 in FIGS. 7 and 8 located generally about 40% of the distance from the bottom surface 78 to the top opening 82.

Four anti-wicking fillets 86 are shown in FIGS. 6–8, best seen in FIG. 7A as dot-dashed lines as there is no sharp delineation between the fillets 86 and the four wall sides above dashed line 87. The anti-wicking fillets 86 are a key feature of the cuvette 24 of the present invention and are formed as a smooth transition that effectively blends the inner corner intersections of front wall 70 and side walls 74 and 76 and the inner corner intersections of back wall 72 and side walls 74 and 76. Each anti-wicking wall fillet 86 comprises a curvilinear taper extending from top opening 82 in top section 84 to lower section 80 at dashed line 87 having the shape of a variable blend radius a variable blend radius between front wall 70 and side walls 74 and 76 and back wall 72 and side walls 74 and 76. The radius of curvature of each anti-wicking wall transition fillet 86 gradually increases from a region proximate dashed line 87 to the top inner section 84 of cuvette 24 by about a factor of three to five forming a variable blend radius of curvature. FIG. 6A shows how anti-wicking wall transition fillets 86 blend uniformly into the bottom surface 78 of lower section 80. Consequently, in this first embodiment, the thickness of front wall 70, back wall 72, and side walls 74 and 76 gradually decreases in thickness from the region of dashed line 87 to the top inner section 84. In the lower region 80, a blend 88, shown in dotted lines for purposes of clarity, having a constant radius of curvature equal to the variable blend radius of curvature of anti-wicking transition fillets 86 in the region of dashed line 87 is formed between inner corner intersections of front wall 70 and side walls 74 and 76 and at the inner intersections of back wall 72 and side walls 74 and 76. Blend 88 has a very small radius of curvature so that lower inner section 80 remains generally rectangular, illustrated as bottom surface 78 in the plan view of FIG. 6A. Blend 88 is incorporated into cuvette 24 in order to minimize trapped reaction debris, thereby increasing the efficiency of washing in wash station 67 as well as facilitating release of a cuvette 24 from an injection molding machine during production operations.

Figure 7B:
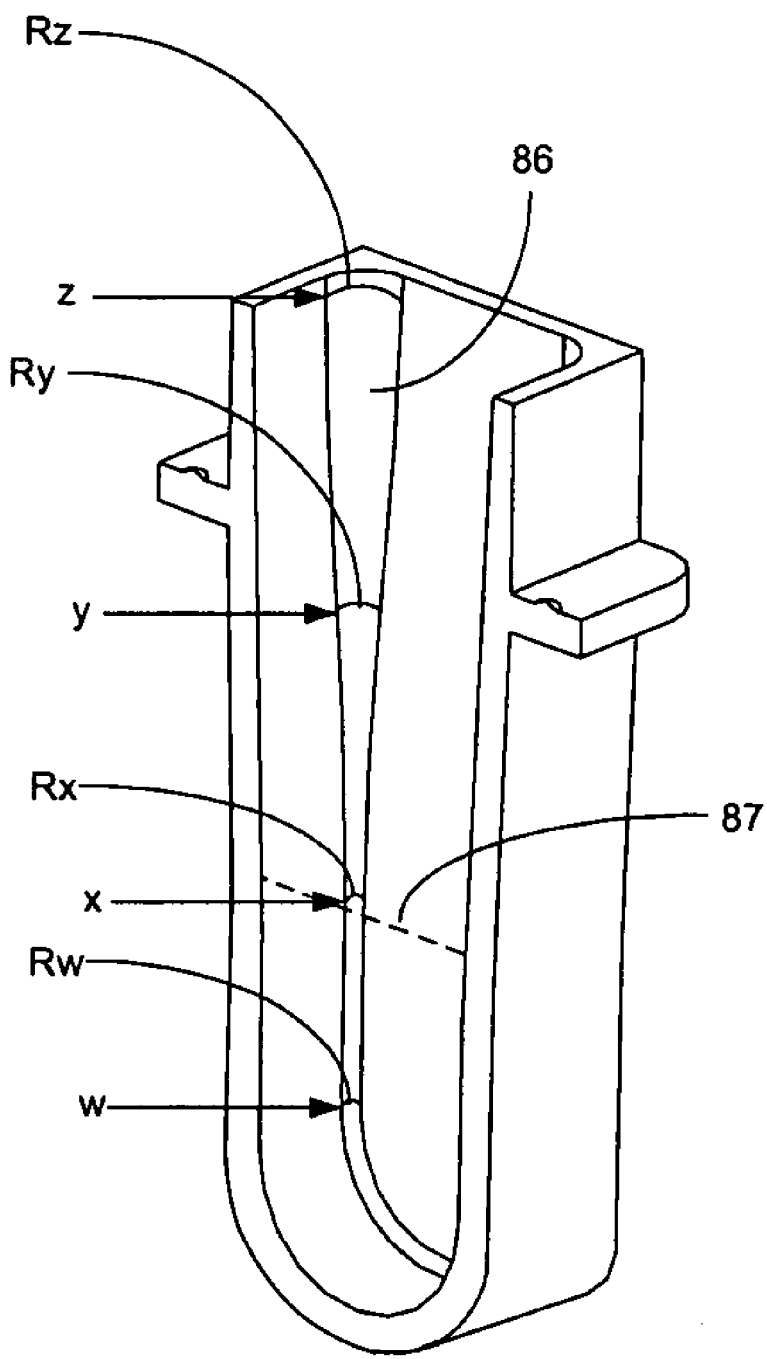
FIG. 7B is a simplified perspective view of the section view of FIG. 7 illustrating certain features of the present invention.

FIG. 7B is a simplified view of cuvette 24 illustrating how the variable blend radius of curvature of each anti-wicking wall transition fillet 86 gradually changes from the region of dashed line 87 to the top inner section 84 of cuvette 24. It has been discovered that if the variable blend radius of curvature of anti-wicking wall transition fillets 86 increases as the distance of the radius increases from the region of dashed line 87, then unwanted wicking is eliminated. In FIG. 7B, for purposes of illustration, the variable blend radius of curvature of each anti-wicking wall transition fillet 86 gradually increases from the region of dashed line 87 to the top inner section 84 of cuvette 24 by about a factor of four times although this factor is not critical. Four location points w, x, y and z are identified as follows:

point w is representative of blend 88 in the lower region 80 of cuvette 24;

point z is representative of the anti-wicking fillet 86 proximate opening 82 in upper region 84 of cuvette 24;

point x is representative of the transition between anti-wicking transition fillet 86 and blend 88 in the region near dashed line 87, about 40% of the distance from the bottom 78 of cuvette 24 in the lower region 80 towards top opening 82 the upper region 84; and, point y is representative of the anti-wicking fillet 86 in a region midway between dashed line 87 and opening 82 in upper region 84 of cuvette 24.

In order to further describe the present invention:

$R_w$ is defined as the variable blend radius of curvature of blend 88 at point w;

$R_x$ is defined as the variable blend radius of curvature of the transition between anti-wicking transition fillet 86 and blend 88 in the region near dashed line 87;

$R_y$ is representative of the variable blend radius of curvature of the anti-wicking transition fillet 86 in a region midway between dashed line 87 and opening 82 in upper region 84 of cuvette 24; and, $R_z$ is representative of the variable blend radius of curvature of the anti-wicking fillet 86 proximate opening 82 in upper region 84 of cuvette 24.

It has been discovered that if the following relations are established between $R_w$, $R_x$, $R_y$, and $R_z$, then the amount of capillary wicking capillary wicking of fluids upwards along the interior surfaces of front wall 70, back wall, and side walls 74 and 76 of cuvette 24 is significantly minimized or totally eliminated:

1. Rw is essentially equal to Rx; and,
2. Ry is generally greater than Rx; and,
3. Rz is generally greater than Ry.

When these relationships between the variable blend radii of curvature of anti-wicking fillets 86 at different heights of cuvette 24 are established, capillary wicking of reagent residues from inside reaction cuvette 24 to an upper surface or outside surface has been found to so completely minimized that cuvette washing by wash station 67 is capable of restoring a used cuvette to the general degree of cleanliness of an unused, new cuvette, and the integrity of reagent solutions is maintained so that accuracy of reaction assays performed therein is not adversely affected. For example, in a particular embodiment in which:

1. Rw is essentially equal to Rx; and,
2. Ry is generally equal to 2Rx; and,
3. Rz is generally equal to 2Ry.

experiments were conducted using colored soap-water in order to aid the optical inspection to ascertain the degree of wicking in cuvettes 24 formed with and without anti-wicking transition fillets 86.

| Relative Variable blend Radius of Curvature | Relative Degree of Colored Soap-Water Wicking |
|---|---|
| 1 | 8 |
| 2 | 6 |
| 3 | 4 |
| 4 | 1 |

It may be reasoned that such effective anti-wicking action is due to the variable blend radius of curvature of the transition fillets 86 increasing in magnitude from Rx in the region of dashed line 87 to Ry essentially equal to 2Rx midway between dashed line 87 and opening 82 to Rz essentially equal to 4Rx proximate opening 82 in the top inner section 84 of cuvette 24; consequently, as fluids within cuvette 24 are drawn upwards by capillary action above the region of dashed line 87, the surface tension between the wall material and the fluid contained within cuvette 24 decreases to the extent that unwanted fluid flow upwards along interior walls of cuvette 24 is significantly minimized if not totally eliminated. In particular, it can be shown that while the height of capillary fluid flow upwards along interior walls of cuvette 24 is directly related to the surface tension between capillary fluid and the materials of construction of interior walls, the height of unwanted capillary fluid flow upwards along interior walls of cuvette 24 is inversely related to the variable blend radius of curvature of the transition fillets 86. Consequently, a key feature of the present invention is that the variable blend radius of curvature of anti-wicking wall transition fillets 86 increases as the location of the radius increases from the region of dashed line 87 so that gravitational forces acting to attract capillary fluid towards the bottom surface 78 of cuvette 24 become greater than the surface tension forces that act to attract capillary fluid towards the top 82 of cuvette 24 thereby causing unwanted wicking to be essentially eliminated. Clearly, if might be desirable to make the variable blend radius of curvature of anti-wicking wall transition fillets 86 proximate opening 82 to be even larger to make unwanted wicking totally impossible; however, there are ancillary constraints upon accessing the inner portion of cuvette 24 with probes, minimizing evaporation losses and analyzer size as well as maintaining a workable volume of fluid within cuvette 24.

It may be seen in FIG. 8 that the thickness (indicated by "a") of front wall 70 and back wall 72 in the lower region 80 and at the junction between lower inner section 80 and the top inner section 84 indicated by dashed line 87 are identical but decrease smoothly to a value (indicated by "b") about 75% of "x" and thereafter decrease smoothly to a value (indicated by "c") about 60% of "a". Similarly, it may be seen in FIG. 7 that the thickness (indicated by "a") of side walls 74 and 76 in the lower region 80 and at the junction between lower inner section 80 and the top inner section 84 indicated by dashed line 87 are identical but decrease smoothly to a value (indicated by "b") about 75% of "a" and thereafter decrease smoothly to a value (indicated by "c") about 60% of "a".

Figure 9:
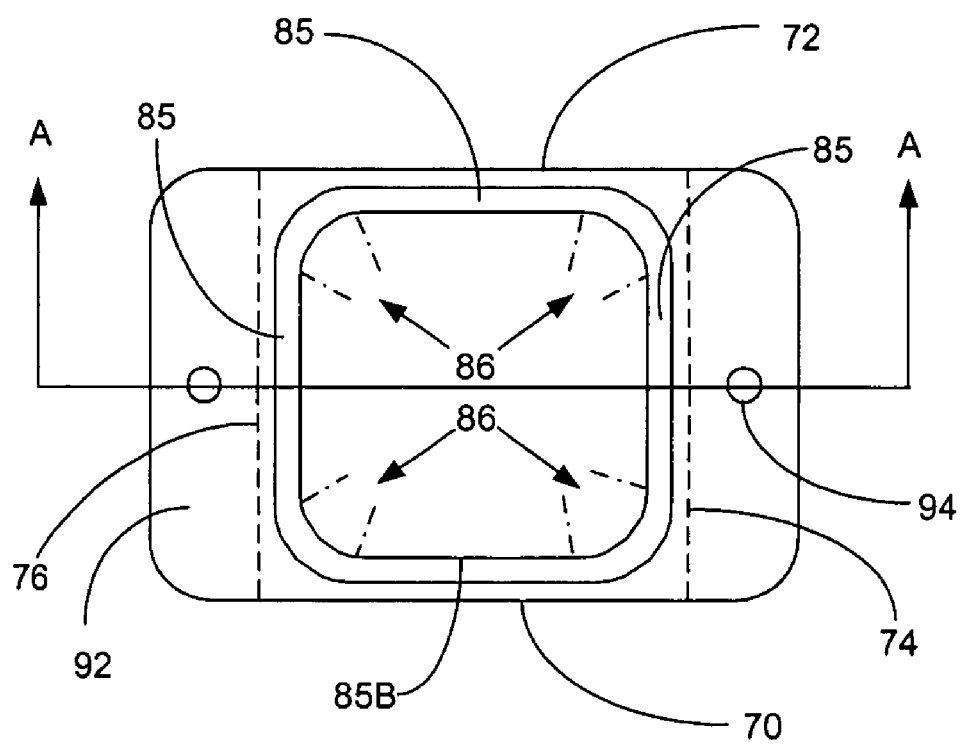
FIG. 9 is a top plan view of an alternate embodiment reaction cuvette illustrative of the present invention.
Figure 10:
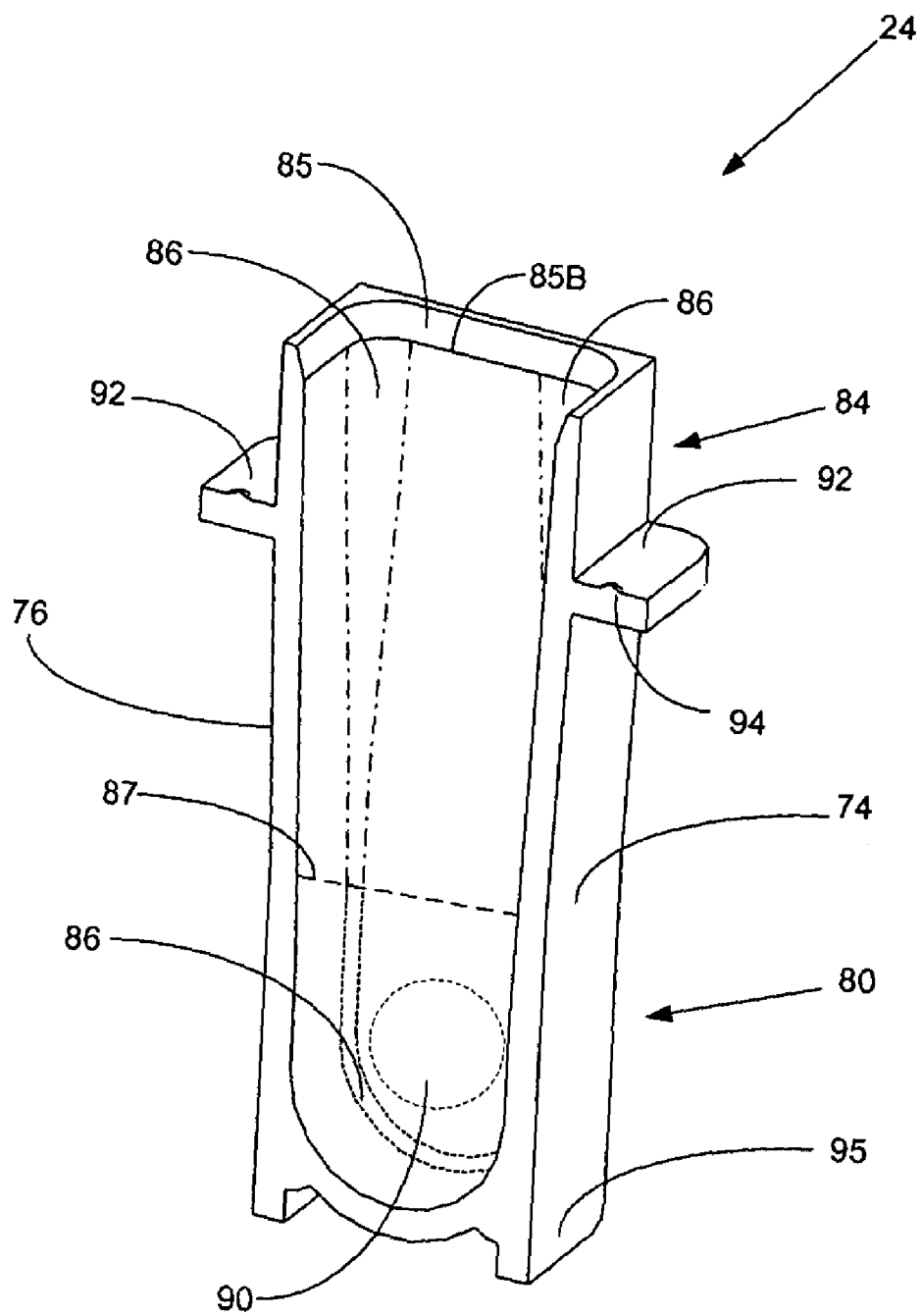
FIG. 10 is a perspective section view of the reaction cuvette of FIG. 9 along the lines A—A.

In an alternate embodiment of the present invention, the uppermost interior portion of front wall 70, back wall 72 and side walls 74 and 76 in top section 84 is shaved to form a downwardly sloped inward chamfer 85 on each of front wall 70, back wall 72, side wall 74 and side wall 76 as best seen in FIG. 9 in combination with FIG. 10. Chamfer 85 is formed at about a 15° angle relative to front wall 70, back wall 72 and side walls 74 and 76 and extends from the top opening 82 of cuvette 24 downwardly a distance approximately equal to the thickness of front wall 70, back wall 72 and side walls 74 and 76. As best seen in FIG. 10, the bottom 85B of chamfer 85 intersects front wall 70, back wall 72 and side walls 74 and 76. In this alternate embodiment, anti-wicking fillets 86 comprise a curvilinear taper extending from the bottom of chamfer 85 in top section 84 to lower section 80 at dashed line 87 forming a rounded concave blend between front wall 70 and side walls 74 and 76 and back wall 72 and side walls 74 and 76. Again, the variable blend radius of curvature of each anti-wicking wall transition fillet 86 gradually increases from a region proximate dashed line 87 to the bottom 85B of chamfer 85 by about a factor of three to five. In this alternate embodiment, similar relations are established between Rw, Rx, Ry, and Rz as listed above, so that capillary wicking capillary wicking of fluids upwards along the interior surfaces of front wall 70, back wall 72, and side walls 74 and 76 of cuvette 24 is also materially eliminated.

Figure 11:
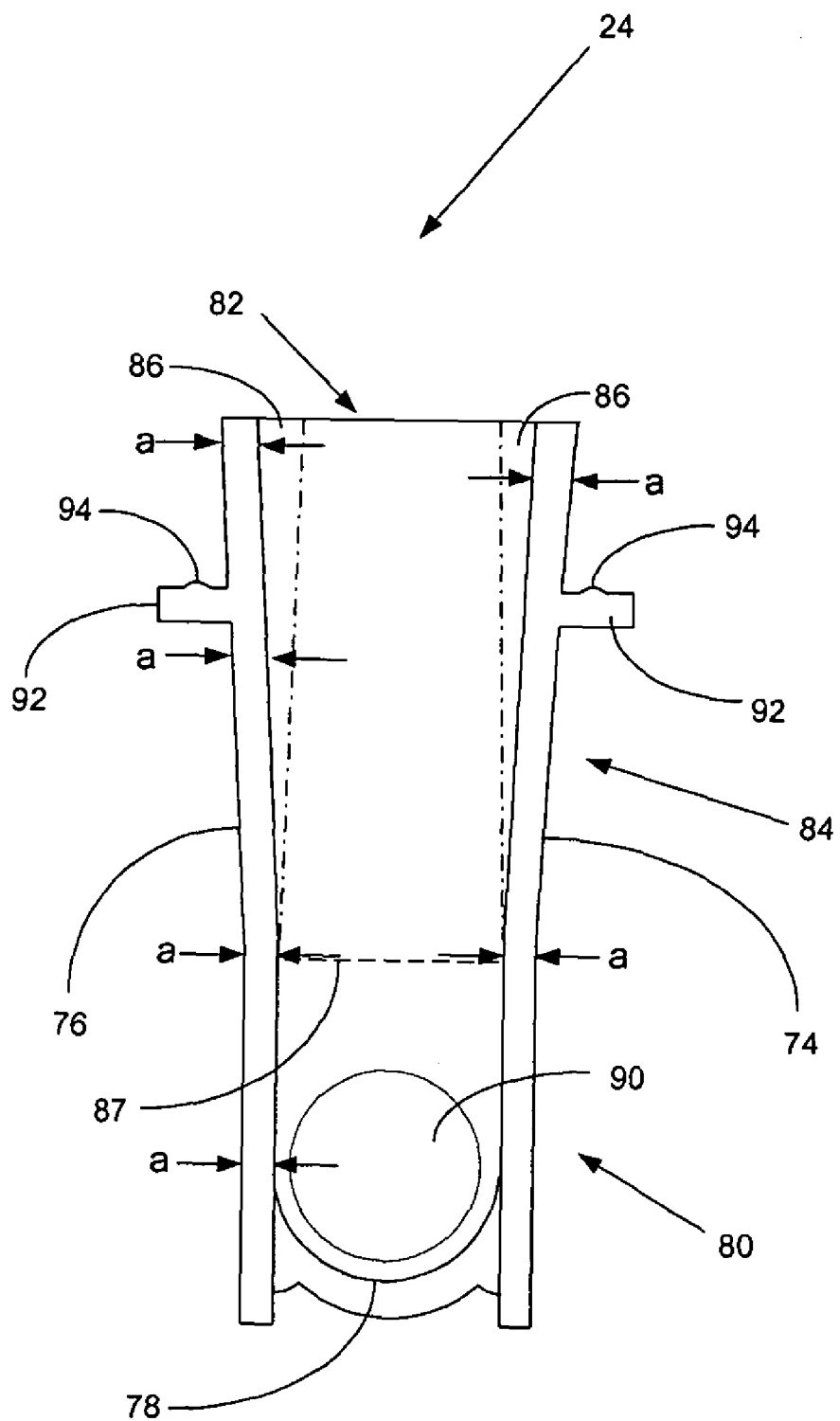
FIG. 11 is a section view of a second alternate embodiment of the reaction cuvette of FIG. 6 along the lines A—A.
Figure 12:
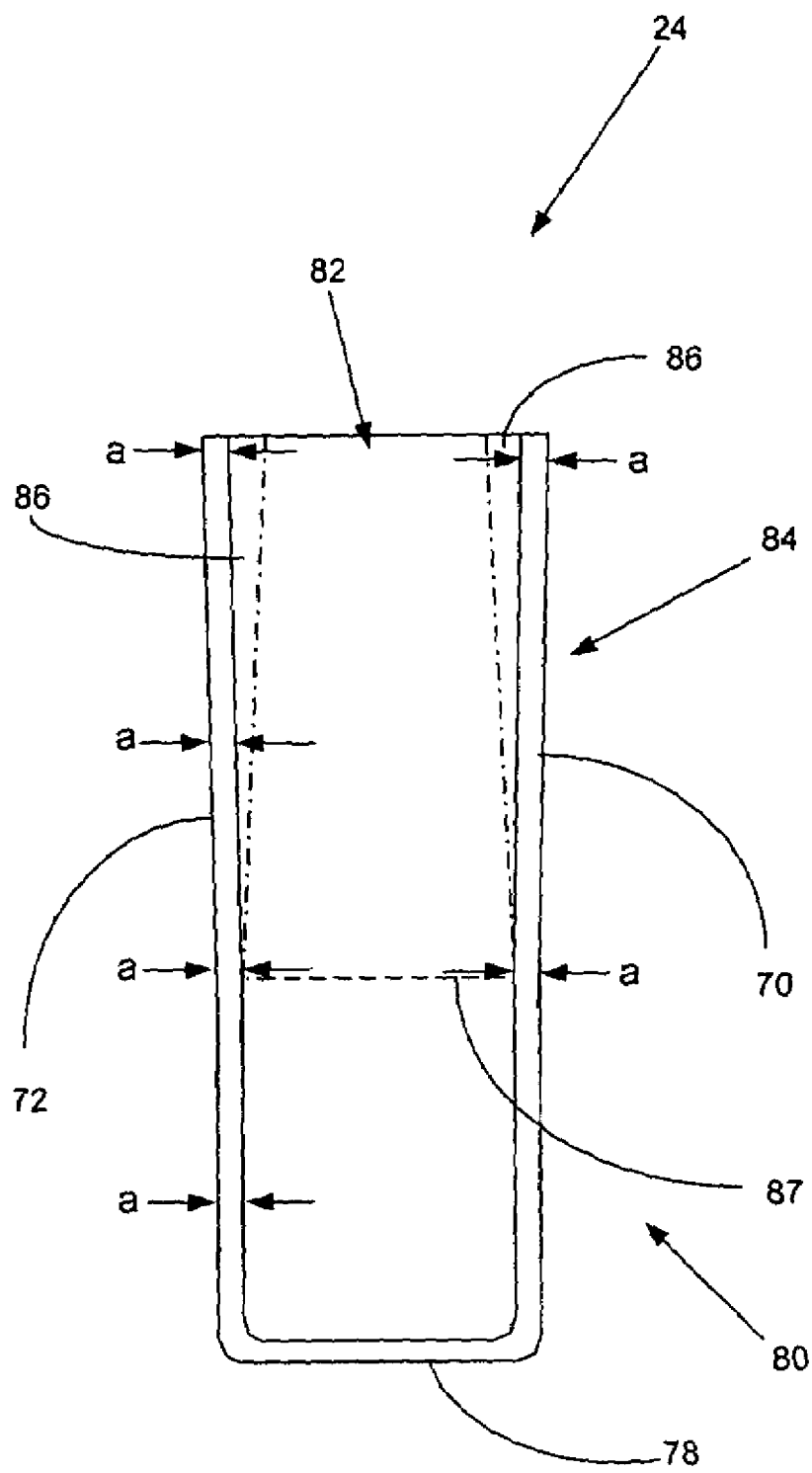
FIG. 12 is a section view of a second alternate embodiment of the reaction cuvette of FIG. 7 along the lines B—B and, FIG. 13 shows an arrangement for supporting the reaction cuvette of FIG. 7 within the analyzer of FIG. 1.

In a second alternate embodiment of the present invention illustrated in FIG. 11, in order to improve molding efficiency, it is desirable that front wall 70, back wall 72, and side walls 74 and 76 of cuvette 24 have a similar thickness. In this instance, side walls 74 and 76 are inclined outwardly, beginning at the dashed line 87 junction between lower inner section 80 and the top inner section 84, a distance so as to maintain an equal wall thickness (indicated by "a"). Similarly, as seen in FIG. 12, front wall 70 and back wall 72 are also inclined outwardly, beginning at the dashed line 87 junction between lower inner section 80 and the top inner section 84, a distance so as to maintain an equal wall thickness (again indicated by "a").

Front wall 70 and back wall 72 are provided with integrally formed opposed angular portions 90 defining planar parallel optical windows 90 for carrying out optical measurements of test sample and reagent mixtures contained within cuvette 24. Each optical window 90 includes outer and inner surfaces of optical flatness one wave over window 90 (4.75 mm), a scratch DIG of 60/20, and minimum 50% transmission between 280 nm and 1000 nm. Birefringence is measured at 300 nm and 600 nm.

Figure 13:
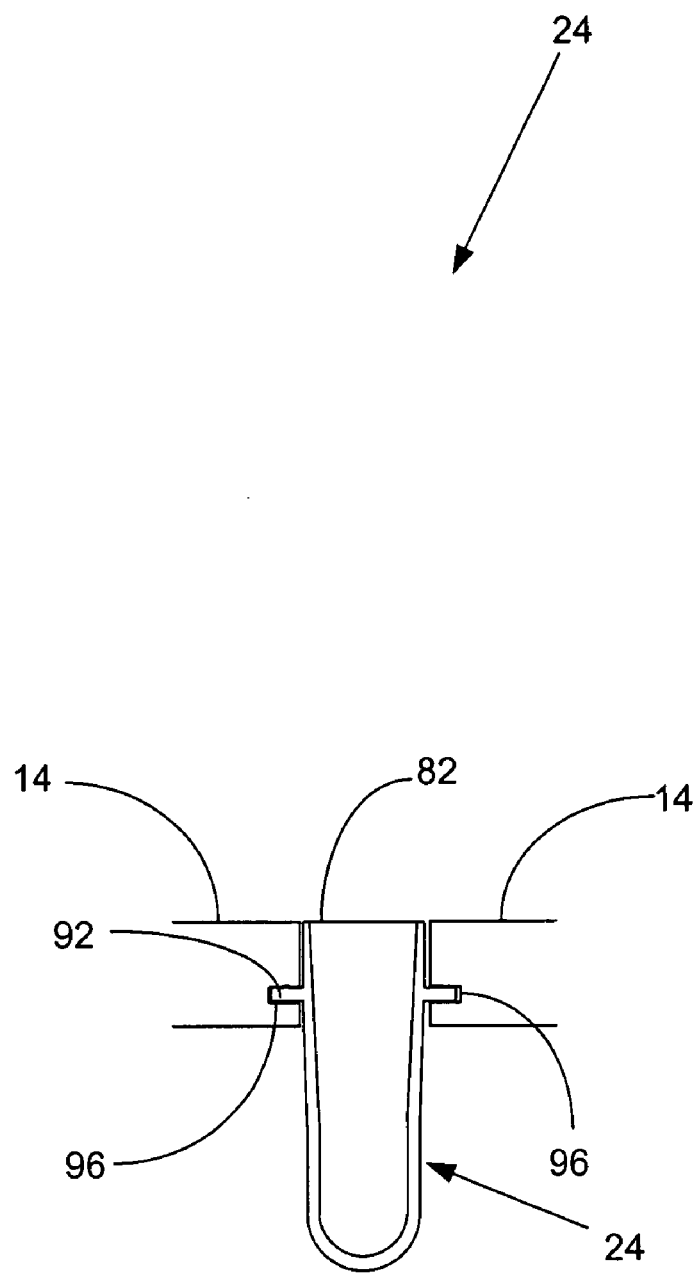

A pair of generally flat, elongate rectangle-shaped ledges 92 are formed in the region of top opening 82 extending outwardly from each of the side walls 74 and 76 in top section 84, with an elongate portion of each lip 92 joined to side walls 74 and 76, as best seen in FIG. 5. In a preferred embodiment, cuvette ports 20 are open on the exterior surface of outer carousel 14 and have a slot 96 opening extending radially outwards a distance downwards from opening 82 at the top of cuvette 24 so that cuvette 24 may be pushed out of a circular cuvette inventory hopper (not shown in FIG. 1) into cuvette port 20 from the side of carousel 14, elongate ledges 92 fitting into slot 96 and top 82 generally flush with the upper surface of carousel 14. This arrangement may be seen in FIG. 13. In addition to providing a supporting surface for holding cuvette 24 in cuvette ports 20, lip 92 further facilitates handling of cuvette 24 by robotic devices unload station 59. An upwardly protruding latching bulge 94 is formed in the central region of each lip 92 to aid in positively positioning and latching cuvette 24 also within cuvette ports 20 as well as within unload station 59.

In an exemplary embodiment, reaction cuvette 24 is formed of polymethylmethacrolate, the inner space of cuvette 24 has a total volume of about 500 microliters, and the optical path length inside dimension between the optical measuring windows 90 is 5 mm. Front and back walls are about 9.5 mm wide and side walls are about 7.0 mm wide. Overall height is about 20 mm with the junction 87 between lower inner section 80 and the top inner section 84 indicated by dashed line 87 being about 8.4 mm above the bottom 82 of cuvette 24. In this instance, dimensions "a", "b", and "c" defined earlier relative to front wall 70, back wall 72, and side walls 74 and 76 are about 1 mm, 0.75 mm, and 0.6 mm, respectively; Rw is about 0.25 mm, Ry is about 0.50 mm and Rz is about 1 mm. The distance between top opening 82 and the bottom 85B of chamfer 85 is about 0.75 mm and in the second alternate embodiment described above, front wall 70, back wall 72 and side walls 74 and 76 are inclined outwardly a distance of about 0.25 mm.

Another feature of the present invention is an optional pair of mutually opposed flat support feet sections 95 formed by the lower end of side walls 74 and 76 extending below curved bottom surface 78 as seen in FIGS. 5 and 10.

It is to be understood that the embodiments of the invention disclosed herein are illustrative of the principles of the invention and that other modifications may be employed which are still within the scope of the invention. For instance, the For these reasons, the present invention is not limited to those embodiments precisely shown and described in the specification but only by the following claims.

We claim:

1. A generally rectangular reaction cuvette comprising mutually opposing front and back walls connected by a pair of mutually opposing side walls, the opposing front and back walls having planar parallel optical windows formed therein, the cuvette having a closed bottom portion and an open top portion, the cuvette further comprising anti-wicking wall fillets blending between the inner corner intersections between the front and back walls and the pair of side walls wherein the anti-wicking wall fillets are curvilinear tapers forming a variable blend radius between the inner corner intersections between the front and back walls and the pair of side walls and wherein the variable blend radius of curvature of each anti-wicking wall transition fillet gradually increases from the lower section to the top inner section by about a factor of three to five.

2. A generally rectangular reaction cuvette comprising mutually opposing front and back walls connected by a pair of mutually opposing side walls, the opposing front and back walls having planar parallel optical windows formed therein, the cuvette having a closed bottom portion and an open top portion, the cuvette further comprising anti-wicking wail fillets blending between the inner corner intersections between the front and back walls and the pair of side walls wherein the uppermost interior portions of the front and back walls and the side walls form a downwardly sloped inward chamfer at about a 15° angle and extending from the top of the cuvette downwardly a distance approximately equal to the thickness of the walls.

* * * * *

UNITED STATES PATENT AND TRADEMARK OFFICE
CERTIFICATE OF CORRECTION

| | |
|---|---|
| PATENT NO. | : 7,138,091 B2 |
| APPLICATION NO. | : 10/623436 |
| DATED | : November 21, 2006 |
| INVENTOR(S) | : Lee et al. |

It is certified that error appears in the above-identified patent and that said Letters Patent is hereby corrected as shown below:

In Claim 2, column 10, line 34 please delete the word "wail" and insert -- wall --.

Signed and Sealed this

Thirtieth Day of January, 2007

JON W. DUDAS
*Director of the United States Patent and Trademark Office*